US010814044B2

(12) United States Patent
Duering

(10) Patent No.: US 10,814,044 B2
(45) Date of Patent: Oct. 27, 2020

(54) IMPLANTABLE OR INSERTABLE MRI-DETECTABLE MEDICAL DEVICE HAVING A COATING COMPRISING PARAMAGNETIC IONS AND A PROCESS FOR PREPARING IT

(71) Applicant: MARVIS INTERVENTIONAL GMBH, Frechen (DE)

(72) Inventor: Klaus Duering, Frechen (DE)

(73) Assignee: MARVIS INTERVENTIONAL GMBH, Frechen (DE)

( * ) Notice: Subject to any disclaimer, the term of this patent is extended or adjusted under 35 U.S.C. 154(b) by 763 days.

(21) Appl. No.: 14/406,663

(22) PCT Filed: Aug. 2, 2013

(86) PCT No.: PCT/EP2013/002318
§ 371 (c)(1),
(2) Date: Dec. 9, 2014

(87) PCT Pub. No.: WO2014/019705
PCT Pub. Date: Feb. 6, 2014

(65) Prior Publication Data
US 2015/0182671 A1    Jul. 2, 2015

(30) Foreign Application Priority Data

Aug. 3, 2012    (EP) .................................... 12005669

(51) Int. Cl.
*A61L 31/10*    (2006.01)
*A61L 31/14*    (2006.01)
*A61L 29/08*    (2006.01)
*A61L 29/18*    (2006.01)
*A61L 27/34*    (2006.01)
*A61M 25/09*    (2006.01)
*A61L 31/08*    (2006.01)

(52) U.S. Cl.
CPC ............... *A61L 31/10* (2013.01); *A61L 27/34* (2013.01); *A61L 29/08* (2013.01); *A61L 29/085* (2013.01); *A61L 29/18* (2013.01); *A61L 31/088* (2013.01); *A61L 31/14* (2013.01); *A61M 25/09* (2013.01); *A61L 2420/08* (2013.01); *A61M 2025/09108* (2013.01)

(58) Field of Classification Search
None
See application file for complete search history.

(56) References Cited

U.S. PATENT DOCUMENTS

| 4,521,564 | A | * | 6/1985 | Solomon | ............. | A61L 33/0029 |
| | | | | | | 523/112 |
| 5,290,894 | A | * | 3/1994 | Melrose | ................. | A01N 35/02 |
| | | | | | | 424/78.08 |
| 5,902,254 | A | * | 5/1999 | Magram | ................ | A61M 25/09 |
| | | | | | | 600/585 |
| 2002/0018898 | A1 | * | 2/2002 | Opolski | ................... | A61L 27/34 |
| | | | | | | 428/423.1 |
| 2003/0099764 | A1 | * | 5/2003 | Li | ......................... | A61K 49/085 |
| | | | | | | 427/2.24 |
| 2004/0092658 | A1 | * | 5/2004 | Qin | ......................... | A61L 15/60 |
| | | | | | | 524/800 |
| 2007/0167735 | A1 | * | 7/2007 | Zhong | .................... | A61L 29/145 |
| | | | | | | 600/410 |
| 2009/0143702 | A1 | * | 6/2009 | Fleischhacker | ....... | A61M 25/09 |
| | | | | | | 600/585 |
| 2010/0063379 | A1 | | 3/2010 | Pfeffer et al. | | |
| 2011/0166439 | A1 | * | 7/2011 | Pfeffer | .................... | A61L 27/50 |
| | | | | | | 600/411 |

FOREIGN PATENT DOCUMENTS

| CA | 2418790 | A1 | 2/2003 |
| DE | 10040381 | C1 | 6/2002 |
| EP | 1206945 | A1 | 5/2002 |
| EP | 1501552 | A | 2/2005 |
| EP | 2450067 | A1 | 5/2012 |
| EP | 2484388 | A1 | 8/2012 |
| WO | 8702893 | A1 | 5/1987 |
| WO | 9849206 | A1 | 11/1998 |
| WO | 9960920 | A2 | 12/1999 |
| WO | 0139814 | A1 | 6/2001 |
| WO | 0222186 | A1 | 3/2002 |

(Continued)

OTHER PUBLICATIONS

Ünaleroğlu, C., et al., "Characterization and magnetic behavior of cobalt(II) and gadolinium(III) polyacrylates", J. Applied Polymer Science, 1995, pp. 1239-1243 (Year: 1995).*
Michinobu, T., et al., "Microparticles of Poly(methacrylic acid)—Gadolinium IonComplex and Their Magnetic Force Microscopic Images",J Polym. Sci. A, 2003, pp. 1912-1918. (Year: 2003).*
Chelating Polymer, accessed from: "https://goldbook.iupac.org/terms/view/CT07154", accessed on Sep. 16, 2019, pp. 1 (Year: 2019).*

(Continued)

*Primary Examiner* — Michael G. Hartley
*Assistant Examiner* — Lance W Rider
(74) *Attorney, Agent, or Firm* — Hultquist, PLLC; Steven J. Hultquist

(57) ABSTRACT

The present invention concerns a medical device detectable by magnetic resonance imaging (MRI), said medical device comprising an envelope polymer that is at least partly removed at the distal end of the medical device wherein said distal end is provided with a coating comprising a coating polymer modified with at least one chemical compound having one or more chemically active free functional groups to provide a surface coating covalently bonded to the free functional groups of the modified coating polymer, wherein paramagnetic ions are encompassed in the coating.

22 Claims, 2 Drawing Sheets

(56) References Cited

FOREIGN PATENT DOCUMENTS

Figure 1:
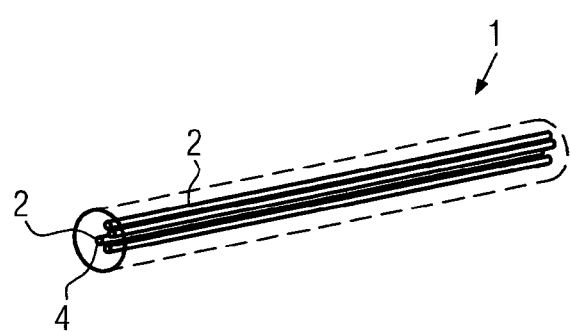

| | | | |
|---|---|---|---|
| WO | 03045462 | A1 | 6/2003 |
| WO | 03094975 | A1 | 11/2003 |
| WO | 2005070475 | A1 | 8/2005 |
| WO | 2007000148 | A2 | 1/2007 |
| WO | 2007080387 | A2 | 7/2007 |
| WO | 2008029082 | A1 | 3/2008 |
| WO | 2009019477 | A2 | 2/2009 |
| WO | 2009038659 | A2 | 3/2009 |
| WO | 2009141165 | A2 | 11/2009 |
| WO | 2012104102 | A1 | 8/2012 |

OTHER PUBLICATIONS

Embed, accessed from: "https://www.merriam-webster.com/dictionary/embed" accessd on Sep. 16, 2019, pp. 1-13 (Year: 2019).*
"Magnetic resonance imaging", Wikipedia. Viewed Mar. 6, 2015. pp. 1-18, Publisher: Wikipedia Foundation Inc., https://en.wikipedia.org/wiki/Magnetic_resonance_imaging.

* cited by examiner

IMPLANTABLE OR INSERTABLE MRI-DETECTABLE MEDICAL DEVICE HAVING A COATING COMPRISING PARAMAGNETIC IONS AND A PROCESS FOR PREPARING IT

CROSS-REFERENCE TO RELATED APPLICATIONS

This application is a U.S. national phase under the provisions of 35 U.S.C. § 371 of International Patent Application No. PCT/EP13/02318 filed Aug. 2, 2013, which in turn claims priority of European Patent Application No. 12005669.2 filed Aug. 3, 2012. The disclosures of such international patent application and European priority patent application are hereby incorporated herein by reference in their respective entireties, for all purposes.

The present invention relates to a medical device and a process for preparing it. In particular, the present invention concerns a medical device which can be detected by means of magnetic resonance imaging (MRI).

A detailed explanation of MRI can be found in the Internet at http://en.wikipedia.org/wiki/Magnetic_Resonance_Imaging.

Medical devices equipped with paramagnetic metallic compounds and/or a paramagnetic metal so that they are visible in MRI are known from EP 1 206 945 A1, WO 99/060920 A2, WO 2003/045462 A, WO 2005/070475 A and WO 03/094975 A. WO 03/094975 A1 outlines a medical device as well as a method of making a medical device magnetic-resonance imagable comprising a coating on the medical device in which a paramagnetic-metal ion/chelate complex is encapsulated by a first hydrogel, a chelate of the paramagnetic-metal-ion/chelate complex being linked to a functional group, and the functional group being an amine group or a carboxyl group. This reference shows a coating for a medical device comprising a paramagnetic ion which is bound in a chelate complex, which itself is covalently coupled to a coating polymer. Furthermore, WO 03/094975 discloses a method that comprises providing a coating on the complete medical device in which a paramagnetic-metal ion/chelate complex is encapsulated. For the methods and devices disclosed in this reference a paramagnetic-metal-ion/chelate complex is a necessary prerequisite.

WO 2005/070475 A1 discloses a medical device with a contrast agent comprising a paramagnetic ion chelation complex, wherein said paramagnetic ion chelation complex is covalently bonded to a hydrogel, coated on a surface of the medical device.

WO 2009/038659 A2 describes organically modified silica nanoparticles with covalently incorporated tetrapyrollic photosensitizers for drug delivery in photodynamic therapy. These nanoparticles may include covalently linked imaging agents, e.g. radionucleotides, MR-imaging agents or fluorescence imaging agents.

WO 87/02893 discloses poly-chelating substances for imaging enhancement and spectral enhancement for MRI. These substances comprise different complexes in which metal ions, in particular gadolinium ions, are immobilized.

The relaxivity of gadolinium(III) complexes is explained in chapter 1.6.1 of the Ph.D thesis (Inaugural Dissertation) by Daniel Storch, entitled "Neue, radioaktiv markierte Magnet-Resonanz-aktive Somatostatinanaloga zur besseren Diagnose und zielgerichteten Radionuklidtherapie von neuroendokrinen Tumoren", Basel, 2005. The paramagnetic relaxation of the water molecules which are present in the vicinity of the gadolinium(III) ion is the result of the dipole-dipole-interaction between the nuclear spin and the fluctuating local magnetic field of the MRI scanner, caused by the unpaired electrons. The magnetic field around the paramagnetic center, i.e. the gadolinium(III) ion, decreases with increasing distance. Therefore, it is essential to locate the protons in close proximity to the metal ion. For gadolinium(III) complexes this means that the water molecules are to be transported into the first coordination sphere of the metal ion. These "inner-sphere" $H_2O$ molecules are exchanged with the surrounding water molecules and in this way transmit the paramagnetic effect.

DE 100 40 381 C2 discloses fluoroalkyl-containing complexes with residual sugars. These complexes can be provided with paramagnetic metal ions so that they can serve as contrast agents in magnetic resonance imaging. These metal ions are in particular the bivalent and trivalent ions of the elements of the atomic numbers 21 to 29, 42, 44 and 58 to 70. Suitable ions are, for instance, the chromium(III), iron(II), cobalt(II), nickel(II), copper(II), praseodymium(III), neodymium(III), samarium(III) and ytterbium(III) ions. Gadolinium(III), erbium(III), dysprosium(III), holmium(III), erbium(III), iron(III) and manganese(II) ions are particularly preferred because of their strong magnetic moment.

WO 99/060920 A, WO 2002/022186 A, WO 03/094975 A and EP 1 501 552 A each show a coating for a medical device comprising a paramagnetic ion which is bound in a chelate complex which itself is covalently coupled to the coating polymer. In particular, the paramagnetic ion is gadolinium. This coating is visible in MRI. Adaptation of the doping of the coating with the gadolinium-chelate complex concurrent with the necessary control of coating thickness and water uptake is difficult to handle. Further, the coating is not stably attached to the surface of the polymer and sensitive to mechanical abrasion. This may lead to the release of coating polymer particles containing gadolinium-chelate complex and result in free flowing of the particles in the bloodstream.

WO 1998/049206, WO 2001/039814, WO 2007/080387, WO 2008/029082 and WO 2009/019477, all of the applicant Polybiomed Ltd., concern different methods how to provide a polymeric surface with hydrophilic properties.

EP 2 484 388 A1 and PCT/EP2012/000514 describe a paramagnetic medical device which is coated on its whole surface with a coating containing an acrolein-acrylic acid copolymer (e.g. a POC compound). In the meantime it has been observed by the inventors that during the necessary extrusion process during production of the medical device water may be split off from the POC compound which gives the surface a bubbly appearance and leads to a more or less coarse surface of the whole medical device. From the standpoint of the potential users, however, a smooth surface is much more desirable since the coarse surface may impair handling of the device. Such a medical device without a perfect smooth surface does not satisfy the expectations of the users for a high quality product. Therefore an additional processing step to obtain a smoother surface would become necessary.

One object of the present invention is to provide a medical device comprising paramagnetic ions which has a smooth surface and is simple to manufacture. These improved medical devices are suitable to be inserted into a human or animal body and are very versatile in their use in MRI examinations.

This object is achieved by a medical device comprising the features of claims 1 and 9. Advantageous embodiments are indicated in the sub-claims.

Throughout the specification the term "medical device" is used in a broad sense to refer to any medicinal device, tool, instrument or other object. The medical devices of the present invention are particularly useful as any type of guidewires, catheters (including vascular and non-vascular, esophageal, peritoneal, peridural, nephrostomy catheters), grafts, biopsy needles, puncture needles, cannulae, intralumenal medical devices, endotracheal tubes, and ablation devices. They can be introduced or implanted in a "target" or "target object". The target or target object is all or a part of the human or animal body. The medical device of the present invention particularly may be brought into cavities of the target (object). These cavities are particularly blood vessels, neuronal ways, any organs (whole or part) or tissues (whole or part).

The medical device of the present invention is characterized by having mechanically stably attached at its distal end a surface coating comprising paramagnetic ions which are directly and strongly encompassed in the surface coating to render the medical device MR visible.

The term "distal" refers to a point located far away from a point of reference (http://www.the_freedictionary.com/distal). With regard to a medical device the term "distal end" has the accepted meaning to refer to that end of the medical device that enters into the target object first.

The basis of the medical device of the present invention may be any MR-safe medical device covered by an envelope polymer, which does not lead to electric conductivity and/or heating and is not dislocated when present in the magnetic and radiofrequency fields during MRI.

Mechanically stable attachment of a coating to the distal end of the medical device is achieved by applying a modified coating polymer which provides chemically active free functional groups. A surface coating is then de novo synthesized by the incubation of at least the distal end of the medical device having the active free functional groups in a solution of one or more surface coating polymers. By the reaction of the functional groups of the one or more surface coating polymers with the active free functional groups of the modified coating polymer the surface coating is covalently bonded. Covalent bonding is the mechanically most stable means of attachment of a coating to a polymer surface of a medical device. This type of surface coating is much superior over the known chelate complexes attached to the surface of the medical device wherein the paramagnetic ion is the central ion in the chelate cage.

Direct encompassing of paramagnetic ions by the surface coating polymer molecules is achieved by constructing a network of polymer layers (at least one, preferably two or more) which contribute free functional groups for encompassing of the paramagnetic metal ion. In contrast to a chelate complex, as used e.g. in WO 03/094975 A1, which is highly symmetric and reproducible, the network for binding of paramagnetic ions according to the present invention is created in a statistical manner, i.e. by formation of a huge variety of different non-symmetric arrangements of functional groups and conformations of these groups in the binding pockets. The binding pockets are "mini-cavities" within the surface coating which are capable to encompass and surround the paramagnetic metal ion. They contribute highest possible stability for encompassing of the paramagnetic ions whereas the binding strength of the paramagnetic ion statistically varies from binding pocket to binding pocket. By the variation of the chemistry of the coating a huge variety of concentrations of the paramagnetic ion, strength of the binding, thickness of the coating and water uptake capacity of the coating can be realized. The washing stringency for the surface coating loaded with the paramagnetic ion may be appropriately chosen to obtain a surface coating with a preset minimum binding stability of the encompassed paramagnetic ions in order to ensure highest possible patient safety, i.e. minimal release of paramagnetic ions.

In a specific embodiment the medical device may comprise at least one rod shaped body (in the following: rod). The rod is preferably a rod as described in WO 2007/000148 A2, WO 2009/141165 A2 or EP application 10 187 863. Therefore, full reference is made to the disclosure of these documents and those documents are incorporated here by reference.

As shown in FIG. 1 the rod 1 comprises one or more non-metallic filaments 2 and a non-ferromagnetic matrix material 3 (in the following: matrix). The matrix material encloses and/or agglutinates the filaments and the matrix material is preferably a regular or high temperature resistant epoxy resin, PVC or synthetic rubber.

For some particular uses the rods or alternatively the envelope polymer may be doped with marker particles for generating a signal in an X-ray or MRI process. These particles (e.g. iron oxide or iron) are embedded in the matrix material or the envelope polymer. Different marker particles may be used, whereas in a medical device differently doped and/or undoped rods or envelope polymers can be incorporated. Simply by use of different markers various medical devices having different characteristics in X-ray or MRI processes can be easily and cost-efficiently manufactured in the same process.

The filaments provide a high strength to the rods in longitudinal direction. Medical devices comprising these rods frequently are designed for being introduced into a blood vessel, an organ (e.g. heart, liver, kidney or lung) or the brain. Therefore, a strong force can be applied to these medical devices in longitudinal direction during introduction of these devices into the body cavity or when pulling them out thereof. This force is taken up by the rods. On the other hand the medical devices have to provide a certain flexibility to guide them along curves of the body cavity.

The filaments are usually made of glass fibers. It is also possible that the filaments are ceramic fibers or polyamide or aramid (e.g. Kevlar®) fibers as long as the fibers provide the necessary strength in longitudinal and lateral direction. It is possible to also use other kinds of fibers as long as the fibers do not provide magnetic and electrically conductive properties.

The rods used for the medical device of the present invention are preferably produced by means of a micro-pultrusion process. In such a micro-pultrusion process a roving (=a group of several filaments being arranged in parallel to each other) is pultruded together with the matrix material in which marker particles, if applicable, can be contained. It is preferred that the number of filaments is at least four or even more, e.g. at least six or at least ten. The amount of filaments has a strong influence on the mechanical properties of the rods. In an alternative embodiment yarns can be used instead of rovings for the production of the rods. In such yarns the filaments are drilled or braided. However, rovings are preferred, as the drilled or braided structure of the yarns may cause a corresponding structure at the surface of the produced rods. Rods having a smooth surface instead of such a structured surface are preferred because it is easier to use them in a subsequent extrusion process.

According to a further aspect of the present invention a medical device comprises one or more rod shaped bodies, each comprising one or more non-metallic filaments and
a non-ferromagnetic matrix material,
wherein the matrix material encloses and/or agglutinates the filaments and marker particles for generating a signal in an X-ray or magnetic resonance imaging process,
and an envelope polymer in which the one or more rod shaped bodies are embedded, wherein a cord is embedded either in the matrix material or in the envelope polymer, wherein the cord is more flexible than the non-metallic filaments.

The cord preferably is a thin cord having a high tensile strength and consists of a material with a higher flexibility than the filaments. Suitable cords are e.g. polyamide filaments, aramid filaments, polyethylene terephthalate (PET) filaments, rayon filaments (e.g. HL fiber), cotton filaments, or hemp filaments. The cord extends along the total device or rod, resp., and is directed in the longitudinal direction of the device or rod, resp. Such a cord does not break if it is bent. This means that if the rod or a medical device incorporating such a rod breaks, the broken parts are still connected by means of the cord. Thereby, it is ensured that even if such a breakage occurs in the human or animal body during the medical intervention the broken parts can be safely pulled out. If the cord is positioned in a rod, it is advantageously arranged in the center of the rod.

In a preferred embodiment the medical device according to the present invention comprises as the envelope polymer a biocompatible material. Such biocompatible materials are available on the market e.g. under the trade names Mediprene® or Tecoflex™. Tecoflex™ is an elastic polymer material which is based on polyurethane (PU). Mediprene® is a thermoplastic elastomer made from SEBS (styrene-ethylene-butylene-styrene-elastomer) which is primarily used for medical purposes. Mediprene may be purchased from Elasto AB, Sweden.

The flexible and elastic envelope polymer provides a certain shape to the medical device. If the medical device is one which contains rods, the envelope polymer encloses the rods. Hence, the medical devices consist of a multi-composite material comprising the rods as a kind of reinforcing material and the envelope polymer as embedding and agglutinating material. The mechanical properties of a medical device are mainly defined by the rods.

According to the present invention a surface coating is covalently coupled to the modified coating polymer of the medical device. This surface coating shall provide a smooth, preferably lubricious, outer surface to the medical device and in a preferred embodiment provide paramagnetic properties.

In a preferred embodiment of the present invention the envelope polymer (e.g. Mediprene® or Tecoflex®) is used to embed and agglutinate the above described rods and/or cords. As mentioned the rods and/or the envelope polymer may be, but need not be, doped with MRI marker particles (e.g. iron or iron oxide) and/or X-ray marker particles. The distal end of this medical device is then ground for the preparation of a coated section whereby the envelope polymer is at least partly or completely removed in this ground section which has a length of about 5 to 50 cm, preferably about 20 to 30 cm. Alternatively grinding may be performed more extensively to further reduce the diameter of the medical device in order to obtain a flexible tip. The flexible tip may have the same length or a shorter length than the section with the ground envelope polymer.

Then a coating solution or suspension, respectively, of a coating polymer, e.g. a polyether block amide copolymer, and a solid or liquid chemical compound having one or more functional groups, preferably amino and/or carboxylic groups, in an organic solvent is prepared. For example, compounds of the PEBAX® series (Arkema, Colombes, France) are suitable as the polyether block amide copolymer. Especially suitable are e.g. PEBAX® 3533 SA01, 4033 SA01, or 2533 SA01, all being thermoplastic elastomers made of flexible polyether and rigid polyamide. The chemical compound having one or more functional groups is selected from mono-, di- or polycarboxylic acids, mono-, di- or polyamines, polyethyleneimine, or polyallylamine. Preferably it is an acrylic acid polymer or an acrolein-acrylic acid copolymer. A suitable example of an acrolein-acrylic acid copolymer is POC AS 5060 (Evonik Industries, Essen, Germany). These chemical compounds hereinafter are called "POC compound". As the organic solvent alcohols or ethers may be used, e.g. 1,1,1,3,3,3-hexafluoroisopropanol, butanol, methylene chloride, or trichloroethylene. The coating polymer and the POC compound may be mixed in the organic solvent to obtain a content of 5, 10, 20, 30 or 40 or higher than 40% (w/w) POC compound within the coating polymer. Preferred is a coating solution or suspension, respectively, containing 70-95% PEBAX® 3533 SA01 and 5-30% POC AS 5060 in 1,1,1,3,3,3-hexafluoroisopropanol, most preferably 80-90% PEBAX® 3533 SA01 and 10-20% POC AS 5060.

As the next step the ground section is coated with the coating solution or suspension, respectively, resulting in a coated distal section. Suitable coating methods may be dip or spray coating but also other coating methods known by the artisan may be suitable. The coated distal section may additionally be ground into a substantially round form to further improve surface smoothness. Preferably this should be done at temperatures below 100° C., e.g. 60-80° C., so that cooling during this grinding process may become necessary. This results in a very smooth surface of the distal section which subsequently is subjected to a surface coating: the functional groups of the modified coating polymer, preferably the carboxyl groups/amino groups, are reacted with corresponding functional groups of a surface coating polymer, preferably with amino groups/carboxyl groups, to obtain a covalent bond, preferably an amide bond. These reactions are according to known peptide chemistry processes and well known to a person skilled in the art. The residual functional groups (e.g. the remaining carboxyl/amine groups) are then at least partially chemically cross-linked by a crosslinker. The surface coating polymer may be a mono-, di- or polyamine or a mono-, di- or polycarboxylic acid.

Examples of "mono-, di- or polyamines" are amino acids (e.g. glycine, lysine, glutamine etc.), ethylenediamine, trimethylenediaminepolyvinylamine, polylysine, 2,4-diaminopropane, 1,3-diaminobutane. Particularly preferred is polyvinylamine (PVA). Examples of "mono-, di- or polycarboxylic acids" are oxalic acid, malonic acid, succinic acid, glutaric acid, adipinic acid, maleinic acid, (poly)acrylic acid, (poly)methacrylic acid, (poly)maleic acid, (poly)aspartic acid, (poly)glutamic acid, alginic acid or pectinic acid. Their linear copolymers, crosslinked copolymers, graft copolymers and block copolymers can be also used and are included within the scope of the invention. Particularly preferred is an acrylic acid polymer or an acrolein-acrylic acid copolymer like POC AS 5060 (Evonik Industries, Essen, Germany). Selection of the crosslinker is not restricted by any limitations. It may be a mono-, bi- or polyfunctional compound. Examples of crosslinking reagents are bifunctional epoxides, isocyanates, chlorotriazines, amidines or aldehydes. In a preferred embodiment of the invention the crosslinking agent is an alcoholic solution of ethylene glycol diglycidyl ether. The amount/concentration of the crosslinker is between 3 and 25%, preferably 10-20%, of the reactive groups.

To provide the medical device with paramagnetic properties the above prepared distal section of the medical device coated with the surface coating is impregnated with an aqueous solution of a paramagnetic marker.

The term "impregnating" means any process for application of an aqueous salt solution to a surface, e.g. dipping, spraying, brushing, soaking etc. The impregnation period is preferably between 20 and 60 minutes, most preferably about 30 minutes.

"Paramagnetic marker" means any chemical compound comprising paramagnetic ions selected from the group of praesodynium (III), neodymium (III), samarium (III), ytterbium (III), gadolinium (III), terbium (III), dysprosium (III), holmium (III) and erbium (III), with gadolinium (III), dysprosium (III) and ytterbium (III) being preferred. Particularly preferred is a Gd(III) chloride solution. Gadolinium, dysprosium and similar metals are passive positive markers as they reduce the proton spin relaxation time of associated water molecules. Due to their specific characteristics and influences on the magnetic properties (relaxation times) of the protons in the water or fat molecules located directly adjacent to the rods or medical devices these MRI markers can be detected by common water or fat proton adjusted MRI sequences. This surface coating may be impregnated with the paramagnetic marker (e.g. gadolinium chloride) solution which binds by the coordination of its free electron pairs to the carboxylic and/or amino groups of the coating. Thereafter, a further layer of surface coating polymer may but need not to be applied and crosslinked. This step may be repeated several times until a thickness of the coating of preferably about 0.05 to 0.10 mm is achieved.

Further optimization with regard to the binding stability of gadolinium may be achieved by (a) using different crosslinkers, (b) variation of the length of the crosslinkers, (c) variation of the concentration of the crosslinkers.

A critical parameter in constructing a valuable and medically useful surface coating is the exchange rate of the water molecules associated with the paramagnetic ions. If the exchange rate is to high the MRI signal may not be recordable at all or may provide a signal at a different location than that of the paramagnetic ion itself as the magnetically enhanced water molecule may have moved away a significant distance during the time period between application of the MR (RF) pulse and measuring of the echo ("echo time"). The flexibility in the design and optimization of the present surface coating allows directed balancing of water uptake and water exchange rates in order to obtain a good MR image without compromising quality of visualization of the body tissue. With respect to passive MRI markers the goal is to have a) a strong signal and b) a confined and sharp signal. However, using passive negative MRI markers, the stronger the signal (artifact) is, the broader are these artifacts which reduces the image sharpness. Preferably, the signal should be reasonably balanced in longitudinal (strong enough) and orthogonal direction (not too broad). The coating containing passive positive MRI markers according to this invention results in an optimally balanced MRI signal in longitudinal and orthogonal direction. Further, due to different physical mechanisms, signals resulting from passive positive MRI markers are easier to separate in image processing from those of the body tissue.

In a particularly preferred embodiment the surface coating of the distal section according to the present invention may contain a further layer of a lubricious polymer which optionally is crosslinked.

Examples of "lubricious polymers" or "surface coating polymers" are poly(L-lysine), polyvinylamine, proteins, collagen, cellulosic polymers, (modified) dextran, gelatin, (carboxymethyl) starch, hyaluronic acid, chitin, polyvinylalcohol, polyvinylpyrrolidone (PVP) or polyvinylpolypyrrolidone (PVPP). The lubricious polymer shall provide a lubricious surface to the distal section of the medical device.

In a preferred embodiment the medical device detectable by magnetic resonance imaging (MRI) comprises an envelope polymer that is at least partly removed at the distal end of the medical device wherein said distal end is provided with a coating of the coating solution or suspension, respectively, of a polyether block amide copolymer, and a polyacrylic acid polymer or an acrolein-acrylic acid copolymer in an organic solvent. In this embodiment it is preferred that the envelope polymer is a polyurethane (e.g. Tecoflex®) or a thermoplastic elastomer made from styrene-ethylene-butylene-styrene-elastomer (e.g. Mediprene®) and the acrolein-acrylic acid copolymer is POC AS 5060, the polyether block copolymer is from the PEBAX® series and the organic solvent is 1,1,1,3,3,3-hexafluoroisopropanol. The polyacrylic acid polymer or acrolein-acrylic acid copolymer contained in the coating solution/suspension is further reacted with a chemical compound having an amino-functional group (e.g. polyvinylamine) after the coating solution/suspension has been applied at the distal end of the medical device to provide a surface coating. Then the surface coating may be impregnated with the paramagnetic ions as described above.

In a related preferred embodiment the coating solution or suspension contains a chemical compound having an amino-functional group (e.g. polyvinylamine), instead of an polyacrylic acid polymer or an acrolein-acrylic acid copolymer, which is reacted with a chemical compound having a carboxyl-functional group (e.g. a POC compound) to provide the surface coating after the coating solution/suspension has been applied at the distal end of the medical device. Then the surface coating may be impregnated with the paramagnetic ions as described above.

In a particularly preferred embodiment the POC compound that is contained in the coating of the distal section is activated and free surface carboxylic groups of the POC compound are reacted with polyvinylamine or other polyamino polymers resulting in a covalent amide linkage. Activation of the coating of the distal section is made with a known activation reagent, e.g. HBTU, HATU, BOP, PyBOP. Free residual carboxylic/amino groups are then crosslinked to provide a stably attached surface coating at the surface of the medical device. Further carboxylic groups may be introduced into the polymeric layers of the surface coating by impregnating the device with a 0.5-5% (preferably 1%) solution of succinic acid anhydride in a suitable organic solvent (e.g. in dimethylformamide). If desired, one or more additional layers of a polyamine (e.g. polyvinylamine) may be brought into the surface coating and at least partially crosslinked. These modified surface coatings are suitable to incorporate paramagnetic markers by impregnating the surface coating with an aqueous solution of a paramagnetic marker, preferably with a 0.5 mg/ml $GdCl_3$ solution. If desired, a further layer of a polyamine as a lubricous polymer (preferably polyvinylamine) may be brought onto the surface of the medical device In other words, polyvinylamine (PVA) is covalently coupled via amide bonds to the carboxylic groups of the POC compound wherein the PVA layer may be provided in a multilayer. Then the PVA layer is slightly crosslinked. Thereafter one or more PVA layers are physically applied and may also be crosslinked. This leads to covalent linkages between the individual layers. The following treatment with succinic acid (butanedioic acid) anhydride provides free carboxylic groups in the PVA coating. This surface coating may then be impregnated with a paramagnetic marker (e.g. gadolinium chloride) solution which binds by the coordination of its free electron pairs to the carboxylic and/or amino groups of the coating. Thereafter, a further PVA layer may be applied and may be crosslinked. This step may be repeated several times until a thickness of the surface coating of preferably about 0.05 to 0.10 mm is achieved.

In another embodiment of the present invention the surface coating is first covalently attached to small polymer particles, e.g. micro- or nano-particles, preferably polystyrene nano-particles. The coated polymer particles are then mixed or compounded with the coating polymer of the medical device which is used to prepare the coating of the ground distal section. Optionally a lubricious coating has to be attached to the surface of the medical device.

The present invention provides the advantage that the compounding and extrusion processes used in PCT/EP2012/000514 for the production of the medical device are avoided. Compounding and extrusion of polymers mostly need temperatures above 150° C. and frequently around 200° C. which may lead to anhydride formation of the POC compound resulting in rough surfaces of the medical device and partial degradation of the POC compound resulting in a reduced number of chemically active free functional groups.

The invention is further described with respect to the Figures which show:

FIG. 1: Rod of a medical device

Figure 2:
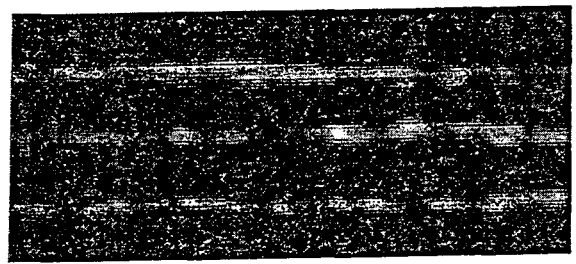

FIG. 2: 3 different test samples resulting in a strong gadolinium-derived MRI signal The invention is further described in the Example:

EXAMPLE 1

A 120 cm guidewire shaft (MaRVis Technologies GmbH, Aachen, Germany) comprising Tecoflex® as the envelope polymer was ground at the distal part over a length of 25 cm. The ground section was dip coated with a suspension of 80% PEBAX® 3533 SA01 (Arkema) and 20% POC AS 5060 (Evonik) in 1,1,1,3,3,3-hexafluoroisopropanol. The resulting coating has a slightly rough surface due to the physical properties of the PEBAX polymer and the coating process. After drying the distal section was ground under water cooling to the same diameter as the guidewire shaft, resulting in a very smooth surface containing the chemically active free functional carboxy groups. Subsequently the ground distal section was coated with PVA as a surface coating polymer by coupling of the free amino groups of the PVA to the free carboxy groups of the coated distal section thereby forming amide bonds.

The PVA surface coating was prepared according to known peptide chemistry processes by reacting polyvinylamine (15% w/v in dimethylformamide) with the HBTU-activated surface of the guidewire. Then the chemical groups at the surface of the guidewire were crosslinked with a 0.7% (v/v) solution of ethylene glycol diglycidyl ether in isopropanol. The guidewire was then dipped into a 1.0% solution of succinic acid anhydride in dimethylformamide.

Subsequently the guidewire was dipped into a 0.25% (w/v) aqueous gadolinium chloride solution and left in the solution until about 4.1 µg gadolinium salt was adsorbed by the surface coating of the guidewire. The decrease of the gadolinium concentration in the aqueous solution was determined according to standard methods. Subsequently a further layer of polyvinylamine was applied as described above. The guidewire was dried in a drying chamber at 80° C.

Surface-coated and gadolinium-loaded test samples were analyzed in an MRI process (c.f. FIG. 2). In these tests the samples were placed in a water bath (water phantom) so that they were completely surrounded and covered by water. This water phantom was placed into the magnetic field of an MR scanner. There are standard measuring conditions ("MR sequences") in MRI systems for detection of the position and properties of the water-protons in the local magnetic field. The samples were tested with the "KM-angio" standard sequence employed on a Siemens Magnetom Symphony 1.5 Tesla MR scanner:

KM-angio Sequence

GRE/FLASH 3D, TR/TE=4.3/1.38 ms, slice thickness: 0.5 mm, FOV=400×325 $mm^2$, matrix: 512×208, averages: 2, phase FOV: 81.25%, percent sampling: 50%, bandwidth: 515 Hz/px, flip angle: 16°, TA=67 s, total number of slices: 88, phase encoding steps: 166 (208), slab thickness: 44 mm

The invention claimed is:

1. A medical device detectable by magnetic resonance imaging (MRI), said medical device comprising an envelope polymer that is at least partly removed at the distal end of the medical device, wherein said distal end is provided with a coating comprising a coating polymer modified by mixture with at least one chemical compound having one or more chemically active free functional groups, to provide a modified coating polymer having said one or more chemically active free functional groups, wherein said one or more chemically active free functional groups have been reacted with functional groups of one or more surface coating polymers to provide a surface coating that is covalently bonded to the modified coating polymer on the distal end of the medical device, wherein the reacted functional groups comprise amino groups and carboxyl groups reacted to form amide covalent bonds, wherein the surface coating contains paramagnetic ions impregnated therein from aqueous solution of a paramagnetic marker so that the paramagnetic ions are encompassed in binding pockets in the surface coating formed by residual carboxylic and/or amino functional groups thereof, the surface coating comprising two or more layers of the one or more surface coating polymers, wherein the paramagnetic ions are bound by coordination of their free electrons to residual carboxylic and/or amino functional groups of the surface coating, and wherein a cord is embedded in and extends essentially along a total longitudinal extent of the medical device.

2. The medical device of claim 1, wherein the coating polymer that is modified with at least one chemical compound comprises a polyether block amide copolymer, and the at least one chemical compound comprises a polyacrylic acid polymer or an acrolein-acrylic acid copolymer.

3. The medical device of claim 1, wherein the envelope polymer is a polyurethane or a thermoplastic elastomer made from styrene-ethylene-butylene-styrene-elastomer.

4. The medical device of claim 1, wherein the at least one chemical compound comprises an acrolein-acrylic acid copolymer.

5. The medical device of claim 1, wherein the one or more surface coating polymers comprise a mono-, di- or polyamine or a mono-, di or polycarboxylic acid.

6. The medical device of claim 1, wherein the one or more surface coating polymers comprise a polyvinylamine.

7. The medical device of claim 1, wherein the paramagnetic ions are selected from the group consisting of ions of gadolinium (Ill), dysprosium (III), praesodynium (III), neodymium (III), samarium (III), ytterbium (III), terbium (III), holmium (III) and erbium (III).

8. The medical device of claim 1, comprising a guidewire, a catheter, a graft, a biopsy needle, a puncture needle, a cannula, an intralumenal medical device, an endotracheal tube, or an ablation device.

9. A process for preparing the medical device of claim 1, comprising at least partially removing an envelope polymer at a distal end of a medical device comprising the envelope polymer, applying to the distal end of the medical device a modified coating polymer comprising a coating polymer modified by mixture with at least one chemical compound having one or more chemically active free functional groups, reacting the modified coating polymer applied to the distal end of the medical device with one or more surface coating polymers having functional groups reactive with the active free functional groups of the modified coating polymer, to provide a surface coating covalently bonded to the modified coating polymer on the distal end of the medical device, wherein the surface coating comprises two or more layers of the one or more surface coating polymers, and wherein the reacted functional groups comprise amino groups and carboxyl groups reacted to form amide covalent bonds, impregnating the surface coating covalently bonded to the modified coating polymer on the distal end of the medical device with paramagnetic ions from an aqueous solution of a paramagnetic marker so that the paramagnetic ions are encompassed in binding pockets in the surface coating formed by residual carboxylic and/or amino functional groups thereof, wherein the paramagnetic ions are bound by coordination of their free electrons to residual carboxylic and/or amino functional groups of the surface coating, and embedding a cord in and extending essentially along a total longitudinal extent of the medical device.

10. The process of claim 9, wherein the coating polymer that is modified with at least one chemical compound comprises a polyether block amide copolymer, and the at least one chemical compound comprises an polyacrylic acid polymer or an acrolein-acrylic acid copolymer, in an organic solvent.

11. The process of claim 9, wherein the envelope polymer is a polyurethane or a thermoplastic elastomer made from styrene-ethylene-butylene-styrene-elastomer.

12. The process of claim 9, wherein the one or more surface coating polymers comprise a mono-, di- or polyamine or a mono-, di or polycarboxylic acid.

13. The process of claim 9, wherein the one or more surface coating polymers comprise a polyvinylamine.

14. The process of claim 9, wherein the paramagnetic ions are impregnated in the surface coating from a gadolinium (III), dysprosium (III), praesodynium (III), neodymium (III), samarium (III), ytterbium (III), terbium (III), holmium (III) or erbium (III) salt solution.

15. The process of claim 10, wherein the organic solvent is 1,1,1,3,3,3-hexafluoroisopropanol.

16. The medical device of claim 1, wherein binding strength of the paramagnetic ions statistically varies from binding pocket to binding pocket in the surface coating.

17. The medical device of claim 1, wherein said cord is embedded in said envelope polymer.

18. A medical device detectable by magnetic resonance imaging (MRI), said medical device comprising an envelope polymer that is at least partly removed at the distal end of the medical device, wherein said distal end is provided with a coating comprising a coating polymer modified by mixture with at least one chemical compound having one or more chemically active free functional groups, to provide a modified coating polymer having said one or more chemically active free functional groups, wherein said one or more chemically active free functional groups have been reacted with functional groups of one or more surface coating polymers to provide a surface coating that is covalently bonded to the modified coating polymer on the distal end of the medical device, wherein the reacted functional groups comprise amino groups and carboxyl groups reacted to form amide covalent bonds, wherein the surface coating contains paramagnetic ions impregnated therein from aqueous solution of a paramagnetic marker so that the paramagnetic ions are encompassed in binding pockets in the surface coating formed by residual carboxylic and/or amino functional groups thereof, the surface coating comprising two or more layers of the one or more surface coating polymers, and wherein the paramagnetic ions are bound by coordination of their free electrons to said residual carboxylic and/or amino functional groups of the surface coating, with a variety of different non-symmetric arrangements of said functional groups and conformations of said functional groups formed in the binding pockets in the surface coating, wherein said binding pockets directly encompass and surround said paramagnetic ions.

19. The medical device of claim 18, wherein binding strength of the paramagnetic ions statistically varies from binding pocket to binding pocket in the surface coating.

20. The medical device of claim 1, said cord therein being flexible and of tensile strength ensuring that if breakage of the medical device occurs in a human or animal body during medical intervention, broken parts of the medical device will be connected by said cord embedded in the medical device, and the broken parts connected by the cord can be safely pulled out of the human or animal body.

21. The medical device of claim 1, wherein said cord is embedded in a matrix material of a rod-shaped body, wherein said rod-shaped body is embedded in said envelope polymer.

22. The medical device of claim 1, wherein each of the two or more layers is at least partially cross-linked by cross-linking carboxylic and/or amino functional groups thereof.

* * * * *

UNITED STATES PATENT AND TRADEMARK OFFICE
CERTIFICATE OF CORRECTION

Page 1 of 1

PATENT NO. : 10,814,044 B2
APPLICATION NO. : 14/406663
DATED : October 27, 2020
INVENTOR(S) : Klaus Düring It is certified that error appears in the above-identified patent and that said Letters Patent is hereby corrected as shown below:

On the Title Page

Under Foreign Application Priority Data:
"(EP)..........12005669" should be -- (EP)...........12005669.2 --.

In the Specification

Column 1, Line 64:
"Diagnose and zielgerichteten" should be -- Diagnose und zielgerichteten --.

Column 2, Line 12:
"DE 100 40 381 C2" should be -- DE 100 40 381 C1 --.

Signed and Sealed this
First Day of December, 2020

Andrei Iancu
*Director of the United States Patent and Trademark Office*